US006200584B1

(12) United States Patent
Rudolph et al.

(10) Patent No.: US 6,200,584 B1
(45) Date of Patent: Mar. 13, 2001

(54) INSECT CONTROL BY INSECT GROWTH REGULATORS BROADCAST BY VOLATILIZATION

(75) Inventors: Robin Rudolph, Grand Prairie; Eric Duffey, Farmers Branch, both of TX (US)

(73) Assignee: Wellmark International, Bensenville, IL (US)

( * ) Notice: Subject to any disclaimer, the term of this patent is extended or adjusted under 35 U.S.C. 154(b) by 0 days.

(21) Appl. No.: 09/452,845

(22) Filed: Dec. 23, 1999

(51) Int. Cl.[7] .......................... A01N 25/00; A01N 37/00; A01N 37/06

(52) U.S. Cl. .......................... 424/405; 514/529; 514/549

(58) Field of Search .......................... 424/405; 514/529, 514/549

(56) References Cited

U.S. PATENT DOCUMENTS

| | | | | |
|---|---|---|---|---|
| D. 365,392 | | 12/1995 | VanGundy et al. | D23/369 |
| 4,751,225 | | 6/1988 | Nishida et al. | 514/277 |
| 5,066,482 | * | 11/1991 | Kohn et al. | 424/45 |
| 5,396,730 | | 3/1995 | VanGundy et al. | 43/131 |

OTHER PUBLICATIONS

Staal et al, Cockroach control with juvenoids, ACS Symp. Ser., 1985, 276 (Bioregul. Pest Control), 201–18.*

Comfort House, MosquitoContro product info, http://www-.comforthouse.com/comfort/mosrepprod.html (downloaded Nov. 18, 1999).

* cited by examiner

*Primary Examiner*—Jose' G. Dees
*Assistant Examiner*—Alton Pryor
(74) *Attorney, Agent, or Firm*—Townsend and Townsend and Crew LLP

(57) ABSTRACT

Insect control through the use of an insect growth regulators is achieved by volatilization of the active compound from a point source in a spatial region such as a room, to diffuse through the air in the region toward objects in the region such as a carpet or a piece of furniture. The ability of the insect growth regulator to retain its activity when applied in this manner, even after periods of time in excess of one month following volatilization, is surprising in view of pre-existing methods of application that involved application of the insect growth regulator directly to the surface or object of interest in liquid form.

16 Claims, No Drawings

INSECT CONTROL BY INSECT GROWTH REGULATORS BROADCAST BY VOLATILIZATION

BACKGROUND OF THE INVENTION

1. Field of the Invention

This invention lies in the field of insect growth regulators and methods of application for the control of insects.

2. Description of the Prior Art

Insect growth regulators (including juvenile hormones) are well known for their use and efficacy in controlling or eliminating insect infestation in humans, in animals, and in both residential and industrial environments. Many types of insects are controllable by insect growth regulators, including fleas, flour beetles, cigarette beetles, and cockroaches. The regulators vary widely in chemical composition, and two of the more prominent classes are are 2,4-dienoic acids and phenoxyphenoxy compounds, particularly phenoxyphenoxyalkoxyheterocyclics, as well as benzoylureas and triazine derivatives. Examples of 2,4-dienoic acids and related compounds are methoprene, hydroprene, neotenin, and epiphenonane. Examples of phenoxyphenoxy compounds are fenoxycarb and pyriproxyfen. Examples of benzoylureas are lufenuron, diflubenzuron, terflubenzuron, triflumaron, hexaflumaron, and flucycloxuron. An example of a triazine derivative is 2-cyclopropylamino-4,6-bis (dimethylamino)-s-triazine.

Insect growth regulators are typically applied in liquid form, either as emulsifiable concentrates that are diluted and then sprayed, or as aerosols. The propellants and solvents that are needed to facilitate these methods of application, however, are increasingly subject to regulatory control, and in many cases this has resulted in a reduction in the performance and the aesthetics of the use of these materials.

SUMMARY OF THE INVENTION

It has now been discovered that insect growth regulators can be applied in a volatilized form to diffuse through air to regions where potential insect infestation exists, and still achieve effective results in insect control. In particular, it has been discovered that a liquid formulation of an insect growth regulator when heated by simple means, such as by being placed on the surface of or in close proximity to an incandescent light bulb or by conventional heating elements of various kinds, will generate a volatilized form of the insect growth regulator that will broadcast itself through a room or other spatial region to effectively condition the region to prevent or at least substantially reduce the maturation of insects from pre-adult stages. Once treated in this manner, insect control will be maintained in the room for an extended period of time. Objects in the room such as carpets, draperies, upholstered furniture, cushions and the like will no longer be active sites for insect growth, even though they may be several feet removed from the volatilization source or at the opposite side of the room.

These and other objects, advantages, features and embodiments of the invention will be more readily apparent from the descriptions below.

DETAILED DESCRIPTION OF THE INVENTION AND SPECIFIC EMBODIMENTS

One class of compounds that can be volatilized for effective broadcast application in accordance with this invention are 2,4-dienoic acids, including salts and esters of the acids, having the formula 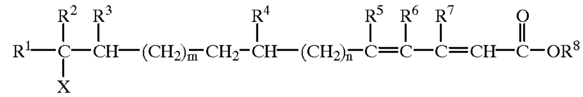 in which:

$R^1$ is $C_1$–$C_6$ alkyl;

$R^2$ is either H, methyl, or ethyl;

$R^3$ is either H or methyl;

$R^4$ is either methyl or ethyl;

$R^5$ is either H or methyl;

$R^6$ is either H or methyl;

$R^7$ is either methyl or ethyl;

$R^8$ is either H, $C_1$–$C_6$ alkyl, $C_3$–$C_6$ alkenyl, $C_3$–$C_6$ alkynyl, $C_3$–$C_8$ cycloalkyl, phenyl, naphthyl, $C_7$–$C_{12}$ aralkenyl, or a cation of lithium, sodium, potassium, calcium, strontium, copper, manganese, or zinc;

X is either Br, Cl, Fl, or $OR^9$, in which $R^9$ is either H, $C_1$–$C_6$ alkyl or $C_1$-$C_6$ alkanoyl;

m is either zero, 1, 2, or 3; and n is either zero, 1, 2, or 3.

In this specification and the appended claims, the term "cycloalkyl" refers to a saturated hydrocarbon ring, including rings with one or more alkyl groups branching off from a ring carbon. Examples are cyclopropyl, cyclopentyl, cyclohexyl, methylcyclohexyl, and cyclohexylmethyl. Preferred cycloalkyl groups are $C_3$–$C_6$ cycloalkyl, with cyclopentyl and cyclohexyl particularly preferred. The term "aralkyl" refers to an alkyl group substituted with an aromatic group both with and without one or more additional alkyl groups branching off from a ring carbon. Examples of aralkyl groups are benzyl, phenylethyl, naphthylmethyl, and ethylbenzyl. Preferred aralkyl groups are $C_7$–$C_9$ aralkyl, with benzyl and phenylethyl particularly preferred. The term "alkanoyl" refers to an alkyl group bonded to a carboxy group. Examples are acetyl, propionyl, butyryl, and hexanoyl. Preferred alkanoyl groups are $C_1$–$C_3$ alkanoyl, with acetyl and propionyl particularly preferred.

Within the scope of the above formula for 2,4-dienoic acids, salts and esters, certain groups of compounds of preferred. One such group is that in which the double bonds are in an E,E or Z,E configuration, preferably an E,E configuration. Another group that in which: $R^1$ is methyl or ethyl; $R^2$ is methyl or ethyl; $R^7$ is methyl; $R^8$ is $C_1$–$C_6$ alkyl or $C_3$–$C_6$ alkynyl; X is chloro or $R^9$; m is zero or 1; and n is 1; all other variables as defined above. A third group is that in which: $R^1$ is methyl or ethyl; $R^2$ is methyl; $R^3$ is H; $R^4$ is methyl; $R^5$ is H; $R^6$ is H; $R^7$ is methyl; $R^8$ is $C_1$–$C_4$ alkyl or $C_3$–$C_4$ alkynyl; X is chloro or $R^9$; m is 1; and n is 1; all other variables as defined above. A fourth group is the same as the third, except that $R^9$ is H, methyl, ethyl, isopropyl, t-butyl, or acetyl. A fifth group is also the same as the third, except that $R^9$ is methyl, ethyl, isopropyl, or t-butyl. Specific examples of known compounds within the scope of this formula are 11-methoxy-3,7,11-trimethyldodeca-2,4-dienoate, isopropyl ester (known by the generic name methoprene, and preferably the isomer trans(2), trans(4)-isopropyl 11-methoxy-3,7,11-trimethyldodeca-2,4-dienoate, or (E,E)-(7S)-11-methoxy-3,7,11-trimethyldodeca-2,4-dienoate, isopropyl ester, known as S-methoprene); 3,7,11-trimethyldodeca-2,4-dienoate, ethyl ester (known by the generic name hydroprene, and preferably the isomer (E,E)-(7S)-3,7,11-trimethyldodeca-2,4-dienoate, ethyl ester, known as S-hydroprene); and 2-propynyl (E,E)-3,7, 11-trimethyldodeca-2,4-dienoate (known by the generic name kinoprene). Methoprene and particularly (S)-methoprene are of particular interest. In the case of hydroprene, the preferred optical configurations are (R,S) and (S), while for kinoprene the preferred configuration is (S).

Another class of compounds that can be volatilized for effective broadcast application in accordance with this invention are 2-pyridyloxy-(lower alkylene)oxy-phenoxy compounds of the formula <img> in which:

$R^{11}$ is either an oxygen atom, a sulfur atom, or a methylene group;

$R^{12}$ is either a hydrogen atom or a methyl group;

$R^{13}$ is either a hydrogen atom or a methyl group;

$R^{14}$ is either an oxygen atom, a sulfur atom, or a methylene group;

$R^{15}$ is either an oxygen atom, a sulfur atom, or a methylene group;

$R^{16}$ is either a hydrogen atom or a fluorine atom; and $R^{17}$ is either a hydrogen atom or a fluorine atom.

Within this formula as well, certain groups of compounds are preferred. In one such group, $R^{11}$, $R^{14}$, and $R^{15}$ are either oxygen or sulfur atoms, and preferably all are oxygen atoms. In another group, $R^{16}$ and $R^{17}$ are both hydrogen atoms. A specific example of an insect growth regulator within the scope of this formula is 2-pyridyloxy-(lower alkylene) oxyphenoxy compound is 2-{1-methyl-2-(4-phenoxyphenoxy)-ethoxy}pyridine (known by the generic name pyriproxifen).

In the practice of this invention, the insect growth regulator is volatilized from a liquid form such as a solution, an emulsion, or the undiluted active compound itself. Liquid solutions are particularly convenient, since a properly selected solvent can facilitate the absorption of the active ingredient by a solid absorbent matrix. The matrix may for example be a filter pad or a piece of fabric, or any such material that is readily wetted with the solution. Any solvent can be used that is not itself objectionable when volatilized, either for aesthetic reasons or for physiological reasons such as allergic reactions, carcinogenic effects, or toxicity to humans or animals. Examples of suitable solvents are volatile alcohols, water, alcohol/water mixtures, and organic solvents in general. With some active ingredients, particularly 2,4-dienoic acids, the inclusion of an antioxidant in the solution may be beneficial. Examples of antioxidants are butylated hydroanisole (BHA) and butylated hydroxytoluene (BHT). Insect growth regulators that are liquids at ambient temperature can also be used without solvents.

The absorbent matrix thus wetted can be placed directly on a heating surface, such as an incandescent light bulb, or a conventional heating device of any description that provides controlled heating. Once volatilized, the insect growth regulator will be effective in preventing the maturation of insects in a spatial region surrounding the heating element. The spatial region may be an enclosed room or a partially or fully open space. The size of the spatial region is not critical, and the volume in which insect control is achieved in this manner will vary to some extent with the amount of the insect growth regulator that is volatilized, the temperature of the heating element and possibly the ambient conditions of the room, as well as the choice of particular insect growth regulator itself. In most cases, the typical spatial region will have a volume ranging from about 10 cubic meters to about 1,000 cubic meters, preferably from about 10 cubic meters to about 500 cubic meters, and most preferably from about 15 cubic meters to about 150 cubic meters. The surface temperature of the heating element may also vary, and the choice of the optimum temperature may vary with the active ingredient. In most cases, typical volatilization temperatures will range from about 50° C. to about 150° C., and preferably from about 80° C. to about 125° C.

One of the advantages of this invention is that it can be used to prevent maturation of insects over an extended period of time in various objects in a spatial region in which insect eggs might reside. Objects in the spatial region will retain their ability to prevent insect maturation for extended periods of time, such as a month or more, after their exposure to the volatilized insect growth regulator.

The following examples are offered for illustration only and are not intended to limit to the scope of the invention.

EXAMPLE 1

This example illustrates the efficacy of S-methoprene volatilized by heating from an incandescent light bulb in the control of fleas (*Ctenocephalides felis*).

Testing was performed in a test room measuring 8.5 m (28 ft.) (length)×6.1 m (20 ft) (width)×4.3 m (14 ft.) (height) with a movable partition to reduce the room to the desired size. For this series of tests, the partition was placed in various positions such that the horizontal area of the room was variously:

18.6 m² (200 ft²), resulting in a room volume of 78.4 m³ (2,800 ft³);

27.9 m² (300 ft²), resulting in a room volume of 117.6 m³ (4,200 ft³);

37.2 m² (400 ft²), resulting in a room volume of 156.8 m³ (5,600 ft³); and 46.5 m² (500 ft2), resulting in a room volume of 196 m³ (7,000 ft³).

A single standard 100-watt incandescent light bulb was used as the heating source, and a felt ring that was cut to fit on the top of the light bulb was used as the support for the liquid S-methoprene solution. Three liquid S-methoprene solutions were used as follows:

Solution A: S-methoprene and IRGANOX® L57 (in a weight ratio of 50:1), to achieve a solution of 83.38% S-methoprene by weight. IRGANOX® L57 (Ciba-Geigy Corp., Hawthorne, N.Y., USA) is a liquid aminic antioxidant in the form of an alkylated diphenylamine. No solvents were used.

Solution B: S-methoprene and BHT (in a weight ratio of 50:1), dissolved in a mixture of 1-methoxy-2-propanol and deionized water (in a weight ratio of 84:16) to achieve a solution of 5.2% S-methoprene by weight.

Solution C: S-methoprene and BHT (in a weight ratio of 50:1), dissolved in a mixture of 1-methoxy-2-propanol and Belmay B-5 Fragrance (in a weight ratio of 44:56) to achieve a solution of 5% S-methoprene by weight.

As the infested target, circular pieces of carpet were used. Each piece was 7.6 cm (3 inches) in diameter cut from a 1.3-cm (0.5-inch) pile nylon carpet, and individual circles were placed at distances of 0.61 m (2 ft), 3.0 m (10 ft), and 6.1 m (20 ft) from the light bulb.

The felt ring in each experiment was wetted with 2 g of solution. In the case of Solution A, this resulted in 1.8 g of S-methoprene being applied to the felt ring. In the case of Solutions B and C, this resulted in 0.1 g of S-methoprene being applied to the felt ring. The bulb was turned on for periods of time ranging from 4 h to 120 h. This is referred to below as the "Activation Time." The temperature of the bulb surface at the location of the felt ring was approximately 215° F. (102° C.). In some of the tests, a horizontal barrier was placed above the carpet circles at distances of 5.1 cm (2 inches) or 7.6 cm (3 inches), to simulate penetration of the S-methoprene to difficult-to-reach places such as under furniture. The carpet circles were placed in two positions below the barrier—one in which the center of the carpet circle was 30 cm (12 inches) from the edge of the barrier (identified below as "Position 1"), and the other in which the center of the carpet circle was 7.6 cm (3 inches) from the edge of the barrier (identified below as "Position 2").

After these exposures, the carpet circles were removed from the room, and sprinkled with flea rearing media and infested with 100 viable flea eggs. Similar carpet circles that had not undergone exposure to the volatilized S-methoprene were similarly sprinkled and infested. The exposed (test) and unexposed (control) carpet circles were then placed in a warm (27° C., 80° F.), high humidity (80% relative humidity) room for 35 days to allow any viable flea eggs in the circles to develop to adult fleas. In some of the tests, the carpet circles were allowed to rest for 35 days after removal from the treatment room before being infested with the flea eggs, to test for residual efficacy. In all cases, efficacy was determined by comparing the results from test circles to those from the control circles. The results are listed in Table I.

TABLE I

Test Results Using Methoprene Volatilized by Light Bulb

| Amount of S-Methoprene Volatilized (g) | Room Size (m³) | Activation Time (h) | Efficacy at Indicated Distance from Source | | |
|---|---|---|---|---|---|
| | | | 0.61 m | 3.0 m | 6.1 m |
| 1.8 | 78.4 | 120 | 100% | 100% | 100% |
| 0.1 | 78.4 | 24 | 99% | 99% | 99% |
| 35-Day Residual Effect: | | | | | |
| 0.1 | 78.4 | 24 | 96% | 96% | 97% |
| 0.1 | 78.4 | 4 | Under 2-in. Overhead Barrier: Position 1: 99% Position 2: 96% | | |
| 0.1 | 78.4 | 4 | Under 3-in. Overhead Barrier: Position 1: 100% Position 2: 100% | | |
| 0.1 | 117.6 | 4 | 100% | 99.4% | 99.4% |
| 0.1 | 186.8 | 4 | 100% | 99.6% | 100% |
| 0.1 | 196 | 4 | 95% | 97.3% | 96.5% |

These results show that excellent control was achieved in all cases, including exposures at the lower dosage rate, the residual effect 35 days after the exposure, and exposures obstructed by an overhead barrier.

EXAMPLE 2

This example is a further illustration of the efficacy of S-methoprene volatilized by heating from an incandescent light bulb in the control of fleas. The test was performed in a conventional residential living room with a floor area of 21.5 m² (231 ft²). A single standard 60-watt incandescent bulb was used as the heat source, with a felt ring containing 0.1 g of S-methoprene (using Solution B of Example 1). The temperature of the bulb surface at the location of the felt ring was approximately 200° F. (93° C.). The exposure time (the length of time that the lamp containing the bulb was turned on) was four hours. The carpet circles were placed twenty feet (6.1 m) from the bulb.

After exposure to the volatilized S-methoprene, the carpet circles were each aged (allowed to rest without additional exposure) for 1, 2, 3, or 4 months. They were then challenged by infestation with flea eggs in the same manner as described above in Example 1. The results, expressed in terms of the number of adult fleas emerging after 35 days, are listed in Table II, together with corresponding results from control samples.

TABLE II

Further Test Results Using Methoprene Volatilized by Light Bulb

| | Number of Adult Fleas Emerging From 100 Eggs Months After Treatment→ | | | |
|---|---|---|---|---|
| Sample | 1 | 2 | 3 | 4 |
| Test Samples: | | | | |
| 1 | 2 | 6 | 16 | 4 |
| 2 | 3 | 5 | 1 | 1 |
| 3 | 3 | 2 | 0 | 8 |
| 4 | 2 | 0 | 0 | 4 |
| 5 | 5 | 2 | 0 | 1 |
| 6 | 2 | 4 | 5 | 6 |
| Mean→ (Arithmetic/ Geometric) | 2.8/2.7 | 3.2/1.9 | 3.7/0.7 | 4.0/3.0 |
| Control Samples: | | | | |
| 1 | 53 | 65 | 54 | 78 |
| 2 | 63 | 73 | 67 | 60 |
| 3 | 65 | 66 | 62 | 82 |
| 4 | 58 | 77 | 62 | 61 |
| 5 | 71 | 64 | 59 | 75 |
| 6 | 73 | 73 | 61 | 65 |
| Mean→ (Arithmetic/ Geometric) | 63.8/63.4 | 69.7/69.5 | 60.8/60.7 | 70.2/69.6 |
| Percent Control→ (Arithmetic/ Geometric) | 95.6/95.8 | 95.5/97.3 | 94.0/98.9 | 94.3/95.7 |

These results show that excellent control was achieved in all cases, and treatment is persistent for up to four months.

EXAMPLE 3

This example illustrates the efficacy of S-methoprene volatilized by a water designed for use with mosquito repellents. The heater was an AgRevo heater, 110–120 v, 50–60 Hz, 5 watts, purchased from DBK Espana Household Technologies, and the tests were performed in the same test room used for Example 1, adjusted to a floor area of 18.6 m² (200 ft²), resulting in a room volume of 78.4 m³ (2,800 ft³). The S-methoprene was placed in the heater by wetting a Whatman filter pad consisting of 50% cellulose and 50% glass fiber, the wetting solution consisting of 8.8% (by weight) S-methoprene in neat 1-methoxy 2-propanol. The amount of solution used was 1.2 g, resulting in 0.1 g of S-methoprene in the pad. Carpet circles were used as in the preceding examples, and all other procedures were the same as those in Example 1. Carpet circles were placed at distances of 0.61 m (2 ft), 3.0 m (10 ft), and 6.1 m (20 ft) from the plug-in-heater, with three carpet circles at each location. Three additional carpet circles were retained outside the room to avoid exposure to the volatilized S-methoprene for use as controls. The activation time for the test circles was four hours. Efficacy was determined by comparing the results from the test circles to those from the control circles. The results are listed in Table III.

TABLE III

Test Results Using Methoprene Volatilized by Plug-In Style Insecticide Heater

| Distance From Heater (m) | Adult Flea Emergence (From 100 Eggs) | | % Efficacy (Relative to Control) |
|---|---|---|---|
| | Individual Tests | Average | |
| (control) | 13/14/14 | 13.7 | |
| 0.61 | 0/1/2 | 1 | 92.7 |
| 3.0 | 1/0/0 | 0.3 | 97.8 |
| 6.1 | 1/0/0 | 0.3 | 97.8 |
| | | | Overall: 96.1 |

These results indicate excellent control at all distances from the plug-in heater and are very close to those obtained with the incandescent light bulb as the volatilization medium.

The foregoing is offered primarily for purposes of illustration, it will be readily apparent to those skilled in the art that the quantities, compositions, methods of volatilization, equipment, and other parameters described herein may be further modified or substituted in various ways without departing from the spirit and scope of the invention.

What is claimed is:

1. A method for controlling insect infestation on an object residing in an air-containing spatial region, said method comprising heating a 2,4-dienoic acid insect growth regulator in liquid form by contacting said insect growth regulator with a heated surface at a temperature of from about 50° C. to about 150° C. selected from the group consisting of (a) the external surface of an incandescent light bulb and (b) the surface of an electrically heated heating element, to volatilize said insect growth regulator whereby said insect growth regulator so volatilized diffuses through air in said region to said object in an amount sufficient to prevent the maturation of insects therein from pre-adult stages of growth.

2. A method in accordance with claim 1 in which a plurality of said objects reside in said air-containing spatial region, said air-containing spatial region is from about 10 cubic meters to about 1000 cubic meters, and said method comprises controlling insect infestation in all of said plurality of objects.

3. A method in accordance with claim 1 in which a plurality of said objects reside in said air-containing spatial region, said air-containing spatial region is from about 10 cubic meters to about 500 cubic meters, and said method comprises controlling insect infestation in all of said plurality of objects.

4. A method in accordance with claim 1 in which a plurality of said objects reside in said air-containing spatial region, said air-containing spatial region is from about 15 cubic meters to about 150 cubic meters, and said method comprises controlling insect infestation in all of said plurality of objects.

5. A method in accordance with claim 1 in which said 2,4-dienoic acid has the formula

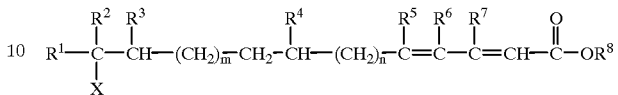

in which:

$R^1$ is $C_1$–$C_6$ alkyl;

$R^2$ is a member selected from the group consisting of H, methyl, and ethyl;

$R^3$ is a member selected from the group consisting of H and methyl;

$R^4$ is a member selected from the group consisting of methyl and ethyl;

$R^5$ is a member selected from the group consisting of H and methyl;

$R^6$ is a member selected from the group consisting of H and methyl;

$R^7$ is a member selected from the group consisting of methyl and ethyl;

$R^8$ is a member selected from the group consisting of H, $C_1$–$C_6$ alkyl, $C_3$–$C_6$ alkenyl, $C_3$–$C_6$ alkynyl, $C_3$–$C^8$ cycloalkyl, phenyl, naphthyl, $C_7$–$C_{12}$ aralkenyl, and cations of metals selected from the group consisting of lithium, sodium, potassium, calcium, strontium, copper, manganese, and zinc;

X is a member selected from the group consisting of Br, Cl, Fl, and $OR^9$, in which $R^9$ is a member selected from the group consisting of H, $C_1$–$C_6$ alkyl and $C_1$–$C_6$ alkanoyl;

m is zero, 1, 2, or 3; and n is zero, 1, 2, or 3.

6. A method in accordance with claim 5 in which:

$R^1$ is a member selected from the group consisting of methyl and ethyl;

$R^2$ is a member selected from the group consisting of methyl, and ethyl;

$R^7$ is methyl;

$R^8$ is a member selected from the group consisting of $C_1$–$C_6$ alkyl and $C_3$–$C_6$ alkynyl;

X is a member selected from the group consisting of Cl and $OR^9$;

m is zero or 1; and n is 1.

7. A method in accordance with claim 6 in which said 2,4-dienoic acid is 11-methoxy-3,7,11-trimethyldodeca-2,4-dienoate, isopropyl ester.

8. A method in accordance with claim 6 in which said 2,4-dienoic acid is (E,E)-(7S)-11-methoxy-3,7,11-trimethyldodeca-2,4-dienoate, isopropyl ester.

9. A method in accordance with claim 6 which said 2,4-dienoic acid is 3,7,11-trimethyldodeca-2,4-dienoate, ethyl ester.

10. A method in accordance with claim 6 which said 2,4-dienoic acid is (E,E)-(7S)-3,7,11-trimethyldodeca-2,4-dienoate, ethyl ester.

11. A method in accordance with claim 1 in which said heated surface is the external surface of an incandescent light bulb.

12. A method in accordance with claim 1 in which said heated surface is the surface of an electrically heated heating element.

13. A method in accordance with claim 1 in which said liquid form is a liquid solution of said insect growth regulator and an antioxidant.

14. A method in accordance with claim 1 in which said insect growth regulator is isopropyl (E,E)-(7S)-11-methoxy-3,7,11-trimethyldodeca-2,4-dienoate and said liquid form is a liquid solution of said insect growth regulator and an antioxidant selected from the group consisting of butylated hydroxyanisole and butylated hydroxytoluene in an organic solvent.

15. A method in accordance with claim 1 in which said insect growth regulator is isopropyl (E,E)-(7S)-11-methoxy-3,7,11-trimethyldodeca-2,4-dienoate and said liquid form is a liquid solution of said insect growth regulator and an antioxidant selected from the group consisting of butylated hydroxyanisole and butylated hydroxytoluene in a solvent comprising a member selected from the group consisting of a volatile alcohol, water, and a mixture of a volatile alcohol and water.

16. A method in accordance with claim 1 in which said method comprises contacting a solid absorbent support matrix wetted with said insect growth regulator in liquid form with said heated surface.

* * * * *

UNITED STATES PATENT AND TRADEMARK OFFICE
CERTIFICATE OF CORRECTION

PATENT NO. : 6,200,584 B1
DATED : March 13, 2001
INVENTOR(S) : Rudolph et al.

It is certified that error appears in the above-identified patent and that said Letters Patent is hereby corrected as shown below:

<u>Title page,</u>
Item [22], after "Filed:" change the date to -- Dec. 3, 1999 --.

Signed and Sealed this

Twenty-seventh Day of November, 2001

*Attest:*

NICHOLAS P. GODICI
*Attesting Officer*   *Acting Director of the United States Patent and Trademark Office*